United States Patent [19]

Chen

[11] Patent Number: 4,676,800
[45] Date of Patent: Jun. 30, 1987

[54] ADJUSTABLE DEVICE FOR ARTIFICIAL LIMBS

[76] Inventor: Sen J. Chen, No. 236, Sec. 3, Ho-Ping West Road, Taipei, Taiwan

[21] Appl. No.: 894,059

[22] Filed: Aug. 7, 1986

[30] Foreign Application Priority Data

Jun. 2, 1986 [TW] Taiwan ............................. 75205777

[51] Int. Cl.[4] .............................................. A61F 2/80
[52] U.S. Cl. ..................................... 623/38; 403/90; 403/61
[58] Field of Search .................. 403/82, 87.61, 90, 91, 403/93; 603/45, 38, 39, 47, 48

[56] References Cited

U.S. PATENT DOCUMENTS

| | | | |
|---|---|---|---|
| 3,273,168 | 9/1966 | Gardner et al. | 623/38 |
| 3,414,908 | 12/1968 | Waggott et al. | 623/38 |
| 3,422,462 | 1/1969 | Finnieston | 623/38 |
| 3,982,278 | 9/1976 | May | 623/38 |
| 4,536,898 | 8/1985 | Palfray | 623/38 |
| 4,608,054 | 8/1986 | Schroder | 623/39 |

Primary Examiner—Richard J. Apley
Assistant Examiner—James Prizant
Attorney, Agent, or Firm—Cushman, Darby & Cushman

[57] ABSTRACT

An improved adjustable device for artificial limbs includes: a cylindrical member having an open section at an upper end for being fixedly coupled with a lower stump portion of an artificial limb, and an annular recess with a plurality of cavities and through openings formed at a lower end; and a coupling member with a mounting piece for being connected to an upper joint portion of an artificial limb and a circular convex protrusion provided on top of the mounting piece with a plurality of screw holes formed in the circular convex protrusion for being coupled with the cylindrical member through a plurality of screw bolts; so that, by adjusting the screw bolts adjustably fixed in the through openings of the cylindrical member, the gravitational equilibrium of the adjustable device can be easily obtained without taking apart the artificial limb incorporated therewith.

3 Claims, 3 Drawing Figures

ADJUSTABLE DEVICE FOR ARTIFICIAL LIMBS

BACKGROUND OF THE INVENTION

This invention is concerned with an adjustable device for artificial limbs, and more particularly with an improved adjustable device by which the gravitational equilibrium of the artificial limb incorporated with this device can be easily adjusted as a user desires.

Many improvements have been made in the construction of artificial limbs, yet there is still much room left to be improvement, particularly in the structure of joints for artificial knees and ankles because of the users' variations in their body dimensions and walking conditions. Generally, both the upper and the lower portions of artificial joints are provided with an adjustable device. As shown in FIG. 1, a typical known adjustable device for an artificial leg includes a sleeve connector B mounted on a positioning pad C round a central tube D of the sleeve connector B and fixed by a plurality of screw bolts A1 to A5, which radially penetrate through the bottom portion of the sleeve connector B, and which have their respective ends abutting against the central tube D of the positioning pad C. For the confort of a user, the sleeve connector B may be positioned as the user desires by first adjusting the screw bolts A1 and A2 located at a bottom side of the sleeve connector B so as to cause the tail ends A11 and A12 of the screw bolts A1 and A2 to disengage with the central tube D, and then tightening the other screw bolts A4 and A5 so as to force the screw bolts A1 and A2 to abut against the central tube D. Consequently, the sleeve connector B is movably inclined a little and its center of gravity is changed accordingly. Apparently, such adjustment is made only for changing the center of gravity of the sleeve connector B. If further adjustment has to be made for satisfying the body equilibrium of the user, the screw bolts A1, A2 and A3 have to be unscrewed and removed from the sleeve connector B for enabling the latter to be disengaged with the positioning pad C, and then the sleeve connector B must be relocated and all the screw bolts A1 through A5 adjusted one by one for properly positioning the sleeve connector B. Finally, the user has to try to walk with the artificial limb to see if it is confortable. If the user finds his center of gravity is not in equilibrium, readjustment has to be made repeatedly.

In addition to the above-mentioned problem, the greater the angular inclination of the sleeve connector B, the less contact the tail ends of some screw bolts (as shown in FIG. 1C) have with the central tube D. Gradually, te tail ends of some screw bolts wear out. As a result, the sleeve connector B may sway slightly, destabilizing the center of gravity and endangering the user's safety as he walks.

SUMMARY OF THE INVENTION

It is accordingly a primary object of this invention to provide an improved adjustable device for artificial limbs that overcomes the problems associated with the prior art.

According to the present invention, this and other objects are achieved through the provision of an improved adjustable device, which comprises: a cylindrical member having an open section at an upper end for being fixedly coupled with a lower stump portion of an artificial limb, and an annular recess with a plurality of cavities and through openings formed at a lower end; and a coupling member with a mounting piece for being connected to an upper joint portion of an artificial limb, and a circular joint flange provided on an top of the mounting piece wit a plurality of screw holes formed in the joint flange for being coupled with the cylindrical member through the annular recess and adjustably connected through a plurality of screw bolts adjustably fixed in the through openings; so that, by adjusting the screw bolts, the gravitational equilibrium of the artificial joints incorporated therewith can be easily and quickly obtained without taking apart of the incorporated artificial limb.

Other advantages and characteristics of the present invention will become clear from the following detailed description of a preferred embodiment when read in conjunction with the accompanying drawings.

DETAILED DESCRIPTION OF THE PREFERRED EMBODIMENT

Figure 1B:
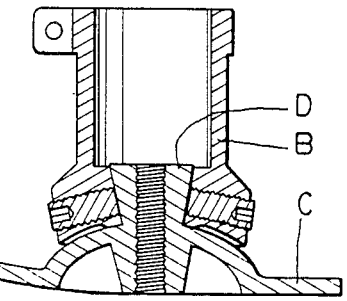
FIG. 1 (A, B, C) are sectional views of a known adjustable device for an artificial limb.
Figure 1B:
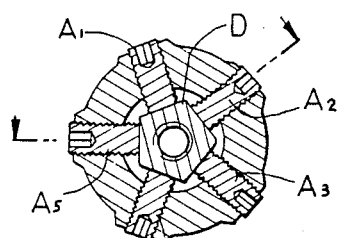
Figure 3:
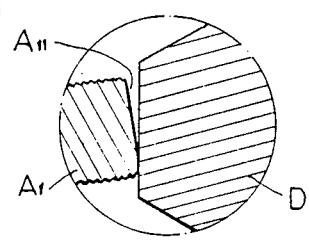
FIG. 3 is an assembled sectional view of the preferred embodiment shown in FIG. 2.
Figure 3:
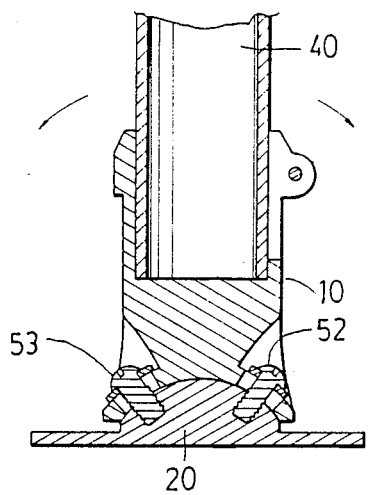
Figure 2:
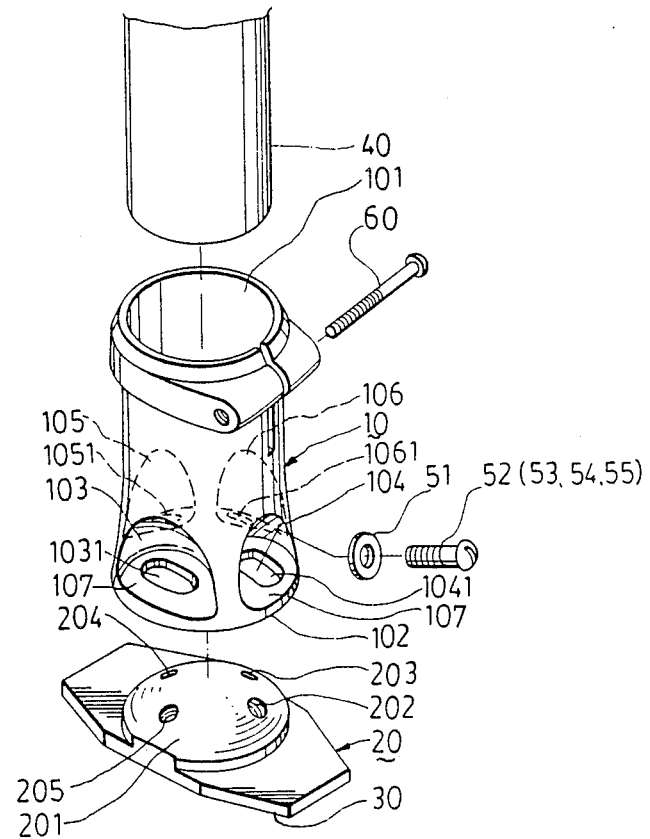
FIG. 2 is a perspective and exploded view of a preferred embodiment of an improved adjustable device for artificial limbs according to this invention.

Referring to FIGS. 2 and 3, the preferred embodient of an improved adjustable device for artificial limbs according to this invention comprises in combination a cylindrical member 10 and a coupling member 20 respectively adapted to be connected to a lower portion and an upper portion of an artificial limb.

The cylindrical member 10 includes: a hollow open section 101 formed at an upper portion for sleeving a lower stump portion 40 of an artificial limb, such as a leg shank, and being secured thereto by a screw bolt 60; an annular recess 102 provided at a bottom side of the cylindrical member 10; a plurality of cavities 103, 104, 105, 106 symmetrically provided in the lower portion with a flat bottom side 107 formed in each one of the cavities; and a plurality of elliptical through openings 1031, 1041, 1051, 1061 respectively located in the bottom side of the cavities 103, 104, 105 and 106, communicating with the annular recess 102.

The coupling member 20 includes a mounting piece 30 for being connected to an upper portion of an artificial limb, such as an ankle of an artificial foot, a circular convex protrusion 201 formed on top of the mounting piece 30 with a plurality of screw holes 203, 204, 205, 206 respectively formed in the flange 201 in conjunction with the elliptical through openings 1031, 1041, 1051 and 1061.

As shown in FIG. 3, the annular recess 102 of the cylindrical member 10 is coupled with the circular convex protrusion 201 of the coupling member 20 and, after properly turning the cylindrical member 10 for ensuring the alignment of the through openings 1031, 1041, 1051 and 1061 with the screw holes 202, 203, 204 and 205, the cylindrical member 10 and the coupling member 20 are adjustably fixed together by a plurality of screw bolts 52, 53, 54, and 55, each of which is matched with a washer 51, through the screw holes 202, 203, 204 and 205.

When the center of gravity of the artificial limb incorporated with the preferred embodiment of this invention is to be adjusted, the user simply loosens the screw bolts 52, 53, 54 and 55 and slightly turns the annular recess 102 along the circular joint flange 201 toward the front or rear, or toward the left or right until the desired angle is reached, then tightens the screw bolts 52, 53, 54 and 55. That is all there is to it simply because the annular recess 102 and the circular joint flange 201 can be easily matched at a satisfactory angle as desired by the user for his gravitational equilibrium without taking apart the artificial limb as needed in the prior art.

Having thus described and illustrated the invention, it is to be understood by those skilled in this art that many embodiments will suggest themselves without departing from the spirit and scope of this invention. Therefore, it is intended the specification and drawings of this invention be interpreted as illustrative rather than in a limiting sense.

What is claimed is:

1. An adjustable device for artificial limbs comprising:

a cylindrical member having a hollow open section at an upper portion thereof for sleeving a lower stump portion of an artificial limb, such as an artificial leg, an annular recess formed on a bottom side thereof for making suitable engagement with an artificial joint, and a plurality of cavities and through openings symmetrically formed around a lower periphery of the cylindrical member; and a coupling member with a mounting piece for being connected to an upper portion of an artificial limb, such as an ankle portion of an artificial foot, and a circular convex protrusion provided on top of the mounting piece with a plurality of screw holes formed in the circular convex protrusion in conjunction with the through openings of the cylindrical member, said circular convex protrusion being coupled with the annular recess of the cylindrical member by a plurality of screw bolts adjustably fixed in the through openings and the screw holes; so that, by adjusting the cylindrical member through the screw bolts, a desired gravitational equilibrium can be easily obtained without taking apart the artificial limb incorporated therewith.

2. An adjustable device for artificial limbs according to claim 1 wherein said through openings are respectively provided in a flat bottom side formed within each one of said cavities and each of said through openings is formed in an elliptical shape for facilitating adjustment therewith.

3. An adjustable device for artificial limbs according to claim 1 wherein each of said screw bolts is coupled with a washer so as to be matched with the elliptical structure of said through openings.

* * * * *